United States Patent [19]

Kohayakawa et al.

[11] 4,293,198
[45] Oct. 6, 1981

[54] EYE REFRACTOMETER

[75] Inventors: Yoshimi Kohayakawa, Yokohama; Yasuyuki Ishikawa, Kawaguchi; Shigeo Maruyama, Kawasaki, all of Japan

[73] Assignee: Canon Kabushiki Kaisha, Tokyo, Japan

[21] Appl. No.: 944,304

[22] Filed: Sep. 21, 1978

[30] Foreign Application Priority Data

Sep. 21, 1977 [JP] Japan ................................ 52/114348
Dec. 1, 1977 [JP] Japan ................................ 52/144309

[51] Int. Cl.³ .................................................. A61B 3/10
[52] U.S. Cl. ........................................ 351/13; 351/14
[58] Field of Search ................................ 351/6, 13, 14

[56] References Cited

U.S. PATENT DOCUMENTS

3,819,256  6/1974  Bellows et al. .................... 351/13 X
3,883,233  5/1975  Guilino ............................. 351/13 X
4,021,102  5/1977  Iizuka ................................. 351/13

Primary Examiner—John K. Corbin
Assistant Examiner—Rodney B. Bovernick
Attorney, Agent, or Firm—Fitzpatrick, Cella, Harper and Scinto

[57] ABSTRACT

An eye refractometer is provided with a projection optical system for projecting test beams forming test patterns such that the central ray of each test beam passes through the pupil of the eye to be inspected while being spaced apart from the optic axis in order to form test patterns corresponding to three meridians forming 60° with each, a focusing lens disposed in the projection optical system and movable only in one direction during one measurement, and a beam detecting device for detecting the reflected images of the test patterns by the retina of the eye and generating electrical signals corresponding to the three meridians.

26 Claims, 24 Drawing Figures

EYE REFRACTOMETER

BACKGROUND OF THE INVENTION

1. Field of the Invention

This invention relates to a refractometer, and more particularly to an apparatus for measuring refractive errors in human eyes.

2. Description of the Prior Art

Machines for manually measuring the refractive values (diopters) of the eyes have long been used and recently, various machines for automatically measuring such refractive values have been proposed.

An auto refractometer is constructed such that with a subject watching a visible object, infrared or near infrared beam is projected upon the retina and the reflected beam therefrom is detected by a photo-detector, and measurement is effected along a plurality of meridians (azimuths) to obtain information on the astigmatism of the eye.

U.S. Pat. Nos. 3,883,233 and 3,888,569 relate to an auto refractometer, and in the former, in order to obtain numerical values for a plurality of meridians, a test figure is rotated through 90° about the optic axis and a focusing lens is reciprocated in the direction of the optic axis for each azimuth and the refractive value is measured from the position of the focusing lens when it is in focus. In the latter, a test pattern projection optical system is rotated through 5° each about the optic axis and the focusing lens is reciprocated for each azimuth and the refractive value is measured from the position of such lens. In this latter apparatus, by paying attention to that the refractive error measured about the optic axis becomes coincident with a sine wave, six values are selected from among numerous measurement data and applied to the sine wave to thereby calculate out exact refractive values except for mechanical errors.

However, in accordance with the mathematical knowledge that the shape of a sine wave is determined by a minimum of three numerical values, the refractive error varied in the form of a sine wave may be determined by three measurement values.

U.S. Pat. No. 4,021,102 controls the position of a test mark by a servo mechanism such that the retina and the test mark are conjugate, and measures three values corresponding to three azimuths by successively selecting three sets of mirrors differing in direction of inclination provided in the projection optical system.

A first common nature of the above-described three patents is that the focusing lens or the test mark is reciprocated in the direction of the optic axis to render the test mark and the retina conjugate. Secondly, to vary the measurement azimuth, it is necessary to provide a mechanically movable member for rotating the test mark or the projection optical system or for sliding the mirror.

On the other hand, Japanese Patent Applications laid open under No. 73491/1975 and 138685/1975 reduce the measurement time by an apparatus which effects measurement by moving a photodetector only once in one direction during one measurement, to thereby reduce the pain of the patient or the subject who must otherwise watch a target for a long time and also reduce the error of measurement which may result from a variation in the refractive power of the eye being inspected during the measurement. However, due to the construction described in these laid open applications in which an image rotating prism provided, in the case of 138685/1975, in the projection optical system is rotated about the optic axis so that the refractive values of the eye about the optic axis are continuously measured, a great number of measurement values must be processed to calculate out information regarding the astigmatism, and also the provision of a mechanically movable member for varying the azimuth leads to the necessity of preventing the irregularity of the rotation of the means for driving such member.

SUMMARY OF THE INVENTION

It is an object of the present invention to enable measurement of a plurality of azimuths without using a mechanically movable member in order to reduce the measurement time and enhance the measurement accuracy.

It is another object of the present invention to enable measurement of a plurality of azimuths by one scanning of a focusing element or elements in one direction of the optic axis.

It is a further object of the present invention to enable measurement of refractive values corresponding to at least three predetermined meridians.

The invention will become more fully apparent from the following detailed description thereof taken in conjunction with the accompanying drawings.

DESCRIPTION OF THE PREFERRED EMBODIMENTS

Figure 1:
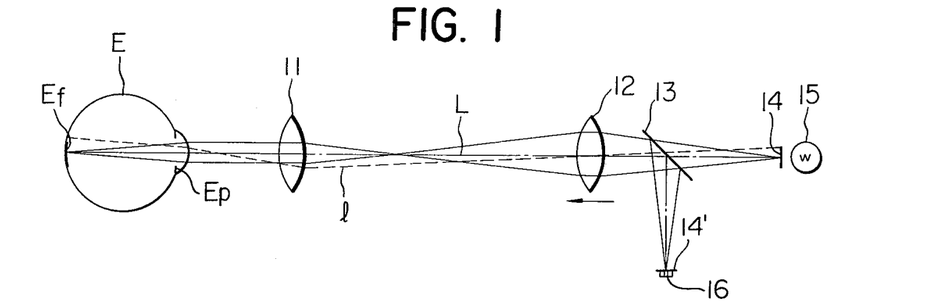
FIG. 1 is a cross-sectional view showing a first specific embodiment of the present invention.
Figure 2:
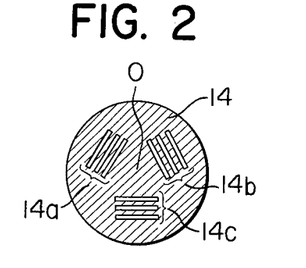
FIG. 2 is a plan view of a mask provided with test patterns.

FIG. 1 depicts the automatic eye refractometer of the present invention. E denotes an eye to be inspected, Ef a retina, and Ep a pupil. Designated by 11 is an objective lens, and 12 a relay lens movable in the direction of optic axis L. The relay lens is moved in one direction in one measurement by a driving mechanism, not shown. The lenses 11 and 12 together constitute a projecting optical system. Denoted by 13 is a half-transparency mirror obliquely disposed with respect to the optic axis, and having a function of uniting together two optic axes. Denoted by 14 is a multiple slits mask which is provided with three sets of slit groups 14a, 14b and 14c as shown in FIG. 2. Each slit group is formed perpendicularly to one of the radii forming 120° with each other, namely, to the meridian forming 60°, and each slit group is spaced apart from the optic axis because the center O of the mask 14 is disposed in coincidence with the optic axis L. These slit groups provide test patterns.

An illuminating light source 15 is provided for uniformly illuminating the mask 14. Designated by 14' is a mask for inspecting the images of the test patterns, which is of the same dimensions and the same shape as the multi-slit mask 14. The mask 14 and the mask 14' are disposed conjugately with respect to the mirror 13.

Figure 3:
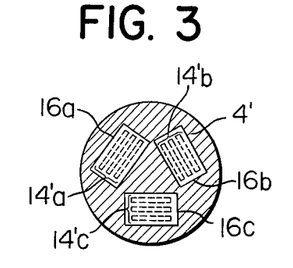
FIG. 3 is a plan view of the mark for inspecting the images of the test patterns.

Designated by 16 is a beam detecting apparatus provided with three light receiving portions 16a, 16b and 16c, as shown in FIG. 3. As the result of the inspecting mask 14' being disposed adjacent to the beam detecting apparatus, the light receiving portions 16a, 16b and 16c overlap the slit groups 14'a, 14'b and 14'c, respectively. The multiple slits mask 14 may be replaced by a transparent plate provided with black bars thereon, and in such a case, the inspecting mask 14' is also replaced by a similar transparent plate provided with black bars thereon.

Description will now be made of the operation of the present invention.

The objective lens is set toward the eye E to be inspected, and then the patient is caused to watch a fixation object, not shown. This is for the purpose of preventing the patient's eye from moving and of maintaining the eye's refractive power constant. When the light source 15 is turned on to illuminate the multiple slits mask 14, the beams passed through the slit groups or test patterns are once focused by the relay lens 12, whereafter the beams are refracted by the objective lens 11 and enter the eye E and are converged by the refractive force of the eye E. If the relay lens 12 is then moved in the direction of the optic axis, the images of the test patterns will also be moved in the direction of the optic axis.

Where the images of the test patterns are formed in front of the retina Ef when the relay lens 12 is in its initial position and where the images of the test patterns are formed behind the retina, there is a position in which the images of the test patterns are formed on the retina Ef in the course of the movement of the relay lens 12.

When the relay lens 12 is in its initial position, the images of the test patterns on the retina Ef are blurred and accordingly, the images formed on the inspecting mask 14' by the beams reflected by the retina Ef and passed through the objective lens 11 and the relay lens 12 and then reflected by the half-transparency mirror 13 is also blurred. Therefore, the images of the test patterns on the slit groups 14'a, 14'b, 14'c of the mask 14' are enlarged and positionally deviated, so that a small quantity of light is passed through the slits and the output signals provided by the beam detecting apparatus are also small. As the relay lens 12 is moved so that the mask 14 and the retina Ef become conjugate, the quantity of light passed through the slits is increased and becomes maximum when the projecting optical system is focused on the retina Ef. If the relay lens is further moved, the quantity of light passed through the slits begins to be decreased and therefore, by tracing the output variation of the beam detecting apparatus and detecting the position of the relay lens 12 on the optic axis at the same time, the refractive value can be measured from the position of the relay lens whereat the maximum output can be obtained. If the three outputs of the beam detecting apparatus assume their maximum values at the same time, there is no astigmatism in the eye being inspected, but if the three outputs assume their maximum values separately, there is an astigmatism in the eye.

In case of an astigmatic eye to be inspected, there can be obtained three positions of the relay lens 12 on the optic axis whereat the signal assumes its maximum value, while on the other hand three meridians are predetermined so that the refractive value corresponding to each meridian can be calculated.

As already mentioned in the Background of the Invention of the present specification, if one approves that the variation of the refractive error of an astigmatism in the direction of the meridian is in accord with sine wave, then the following can be said:

$$D = A \sin(2\theta + \alpha) + B \ldots \quad (1)$$

where D and $\theta$ are variables, D represents a refractive value (diopters), and $\theta$ represents the angle from the reference of the meridian (azimuth). A, B and $\alpha$ are constants, A represents the cylinder power, B the average refractive value, and $\alpha$ the axis (azimuth angle of the astigmatism axis).

In equation (1), there are three unknown quantities and therefore, if there are measured values in three meridian directions, the values of the degree of astigmatism, the average visibility and the direction of the astigmatism axis can be obtained with respect to any desired meridian direction by using the equation (1). By limiting the measured meridian directions not to three but increasing them over three, it is of course possible to enhance the accuracy by obtaining the aforesaid values of any desired three sets thereof and averaging with the values obtained for the other sets.

Figure 4:
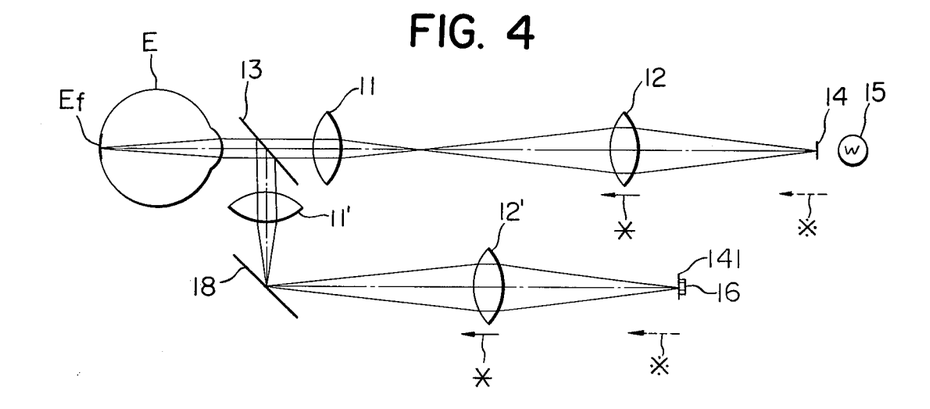
FIG. 4 is a cross-sectional view showing a modification of the FIG. 1 embodiment.

FIG. 4 shows a modification of the first embodiment of the present invention. In this example, a split mirror 13' for splitting the light source and the received light is disposed between the objective lens 11 and the eye E to be inspected. This split mirror may be placed anywhere in the system, but if it is disposed near the light source, the system will be simplified but a problem of reduced SN ratio is caused by the reflection from the lens surface.

The slit mirror 13' may be either of the wave front slit type or the amplitude slit type. In the above-described two embodiments, in order to make conjugate the bottom of the eye to be inspected and the slit plates 14, 14', movable relay lenses 12, 12' are moved, but as an alternative method, the slit plates 14, 14' or the relay lens 12 and the slit plate 14' may be moved to obtain the same effect.

In the embodiments described above, the ray 1 (FIG. 1) passed through the center of the test pattern (slit group) is inclined with respect to the optic axis L so that positional deviation occurs to the image of the pattern by defocusing, and the described embodiments detects the blur of the pattern image, whereas the next embodiment to be described detects the positional deviation of the pattern image.

Figure 5:
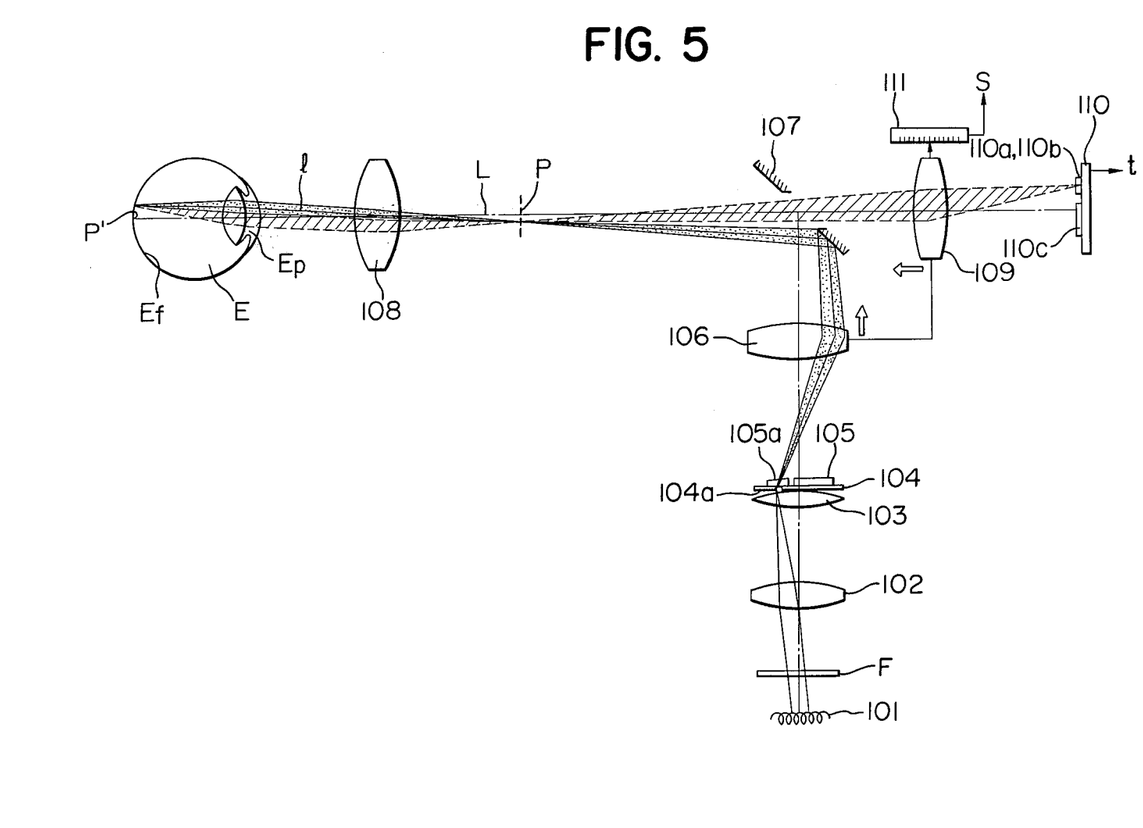
FIG. 5 is a cross-sectional view of a third specific embodiment of the present invention.
Figure 6:
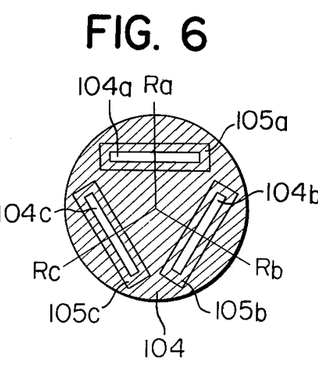
FIG. 6 is a plan view of a multiple slits mask.

Reference will now be had to FIGS. 5 to 11 to describe a third embodiment of the present invention. Designated by 101 is a light source, 102 a condenser lens, 103 a field lens, 104 a multiple slits mask and 105 a triangular prism pillar. The plan view of the slits mask 104 is shown in FIG. 6, in which the slits mask is provided with rectangular slits 104a, 104b and 104c having longer sides orthogonal to the three radii Ra, Rb, Rc forming 120° with each other, and pillar-like prisms 105a, 105b and 105c are attached to the respective slits. These prisms are inclined in the meridian direction and function to refract the beams leaving the slits to separate these beams from one another such that these beams are not mixed together on the pupil. Small lenses may be disposed in place of the prisms to provide a directionality to the emergent light.

Denoted by 106 is a relay lens, and 107 a beam selective mirror which may be one of various types. In the present embodiment, the beam selective mirror is provided by an obliquely disposed mirror having a circular opening formed in the center thereof. Designated by 108 is an objective lens having an optic axis L. This optic axis L provides the measurement axis. Here, the reflecting surface of the mirror 107 is disposed substantially conjugately with the multi-slit mask 104 with respect to the relay lens 106 and conjugately with the vicinity of the pupil Ep of the eye to be inspected.

Members 101 to 108 together constitute a projecting system.

Another relay lens 109 is disposed rearwardly on the axis of the objective lens 108. Denoted by 110 is a detector device. Members 108 to 110 together constitute a detecting system. The projecting system and the detecting system are disposed optically coaxially through the reflecting surface.

Figure 7:
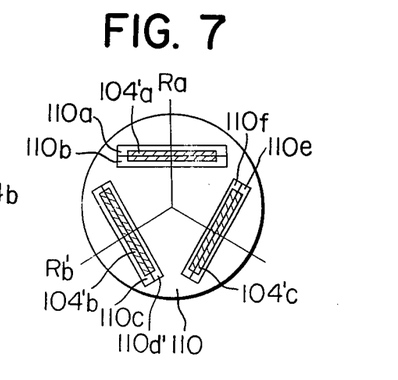
FIG. 7 is a plan view of a beam detecting device.

The plan view of the detector device is shown in FIG. 7, wherein each two light receiving elements having lengthwise light receiving areas perpendicular to radii Ra, Rb, Rc are disposed adjacent to each other, the light receiving elements 110a and 110b, 110c and 110d, and 110e and 110f forming respective sets. The boundary between the adjacent light receiving elements is disposed so as to equally split the image of the slit, in other words, conjugately with the center line of the slit, when the eye bottom Ef and the light receiving surface of the detector device become conjugate with the intervening optical member due to the action which will hereinafter be described.

On the other hand, the relay lenses 106 and 109 are movable in the direction of the optic axis and operatively associated with each other, and the multi-slit mask 104 and the plane containing a point P conveniently given on the optic axis L are always maintained conjugate with respect to the relay lens 106 and the oblique mirror 107, and the light-receiving surface of the detector device 110 and the plane containing the point P are maintained conjugate with respect to the relay lens 109. A point P' is one conjugate with the point P with respect to the objective lens 108 and the eye E to be inspected. If the eye E is an ideal eye, an image is formed on the retina Ef when a parallel beam impinges on the eye and therefore, if the point P is in accord with the focal point of the objective lens 8, the point P' is in accord with the retina Ef and the position of the relay lens at that time is determined as the reference position. If the relay lenses 106 and 109 are made equal in their refractive powers, the amounts of movement of the two lenses may conveniently always be equal. Denoted by 111 is a position detecting device such as potentiometer or the like and it puts out the positional information of the relay lens 109 as an electrical signal S which is applied as input to an electrical processing circuit which will hereinafter be described.

Denoted by F is an infrared filter which passes therethrough the infrared rays of the radiation, passed from the light source 101, to cut off visible lights.

The dotted portion in FIG. 5 indicates a light beam emergent from a slit in the multi-slit mask and 1 designates the center ray thereof. The center ray 1 is spaced apart from the optic axis L on the pupil. The hatched portion indicates the light beam scattered and reflected by the eye bottom and then entering the detecting device.

Operation of the above-described embodiment will now be explained.

The subject is caused to occupy a predetermined position, the objective lens of the refractometer is directed toward the eye E to be inspected, the light source 101 is turned on and the subject is caused to watch an unshown target.

Figure 8:
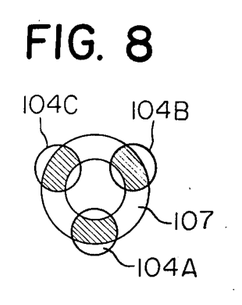
FIG. 8 is a plan view of a beam selective mirror having an opening.

The infrared beam passed through an infrared filter F after having left the light source 101 is condensed onto the multi-slit mask by the lens 102 and illuminates the slits 104a, 104b and 104c. The infrared beam passed through the test patterns, namely, the slits is refracted by the prisms 105a, 105b and 105c and converged by the relay lens 106, whereafter the beam is directed to the oblique mirror 107 provided with an opening, but as shown in FIG. 8, the infrared beams 104A, 104B, 104C passed through the respective slits are suitably separated from one another and reach the mirror 107. In that case, only the infrared beam overlapped with the mirror surface and indicated by the hatching is reflected and after the images of the slits are formed on the plane perpendicular to the optic axis and passing through the point P, the beam is converged by the objective lens 108 and, in case of the reference arrangement, the infrared beam having left the objective lens 108 becomes a parallel beam.

Figure 9:
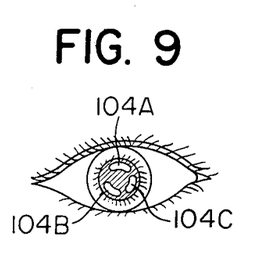
FIG. 9 depicts an eye to be inspected as irradiated with test beams.
Figure 10:
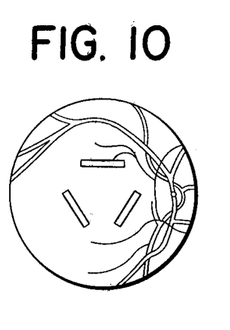
FIG. 10 depicts a retina on which test patterns have beem projected.

FIG. 9 depicts the light beams passing through the pupil of the eye to be inspected and actually, these light beams are invisible to the eye, but they are separated from one another, as shown. When the infrared beams have been converged by the refractive power of the eye itself, each point of convergence is formed on or before or behind the retina in dependence of the refractive power and forms clear slit images as shown in FIG. 10, or forms blurred images. The clear or blurred images on the retina are scattered and reflected and travel back through the eye to be inspected to the objective lens, where the light is converged and then diverged, whereafter it is again converged onto the light receiving surface of the detector device 110 by the relay lens 109.

Figure 11:
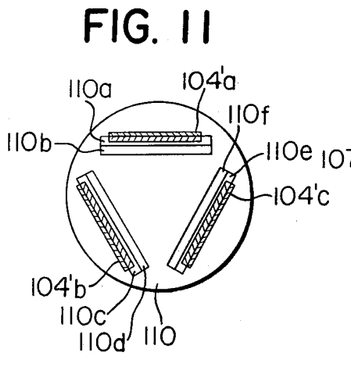
FIG. 11 is a plan view of the beam detecting device on which the defocused images of the test patterns are formed.

FIG. 11 illustrates the relation between the images 104'a, 104'b and 104'c of the test patterns formed on the light receiving surface and the sets of light receiving elements when the test pattern image P' is formed forwardly of the retina due to abnormality of the refractive force. Here, the image is blurred and deviated from the reference position (the position of image formation when the eye is an ideal one), so that a greater quantity of light passes to the outer light receiving elements while a lesser quantity of light passes to the inner light receiving elements, whereby the sets of light receiving elements produce an output difference. The pattern images depicted in FIG. 11 present a substantially equal amount of deviation and this refers to the case where the eye to be inspected has no astigmatism, but the amount of deviation of the pattern images will become irregular when the eye has astigmatism.

When effecting measurement, the relay lenses 106 and 109 are continuously moved toward the oblique mirror 107 and by moving the point P away from the objective lens 108, the point P' is also displaced away from the objective lens 108 and the position detecting device 111 detects the position of the relay lenses at the point of time whereat the pattern images are formed at the reference position of the detecting device. The points of time whereat the output differences of the elements forming the respective sets of light receiving elements may be simultaneous with each other or different from each other and therefore, the positions of the relay lenses at the point of time whereat the output of each set becomes an extremal value must be measured for each meridian direction.

Figure 12:
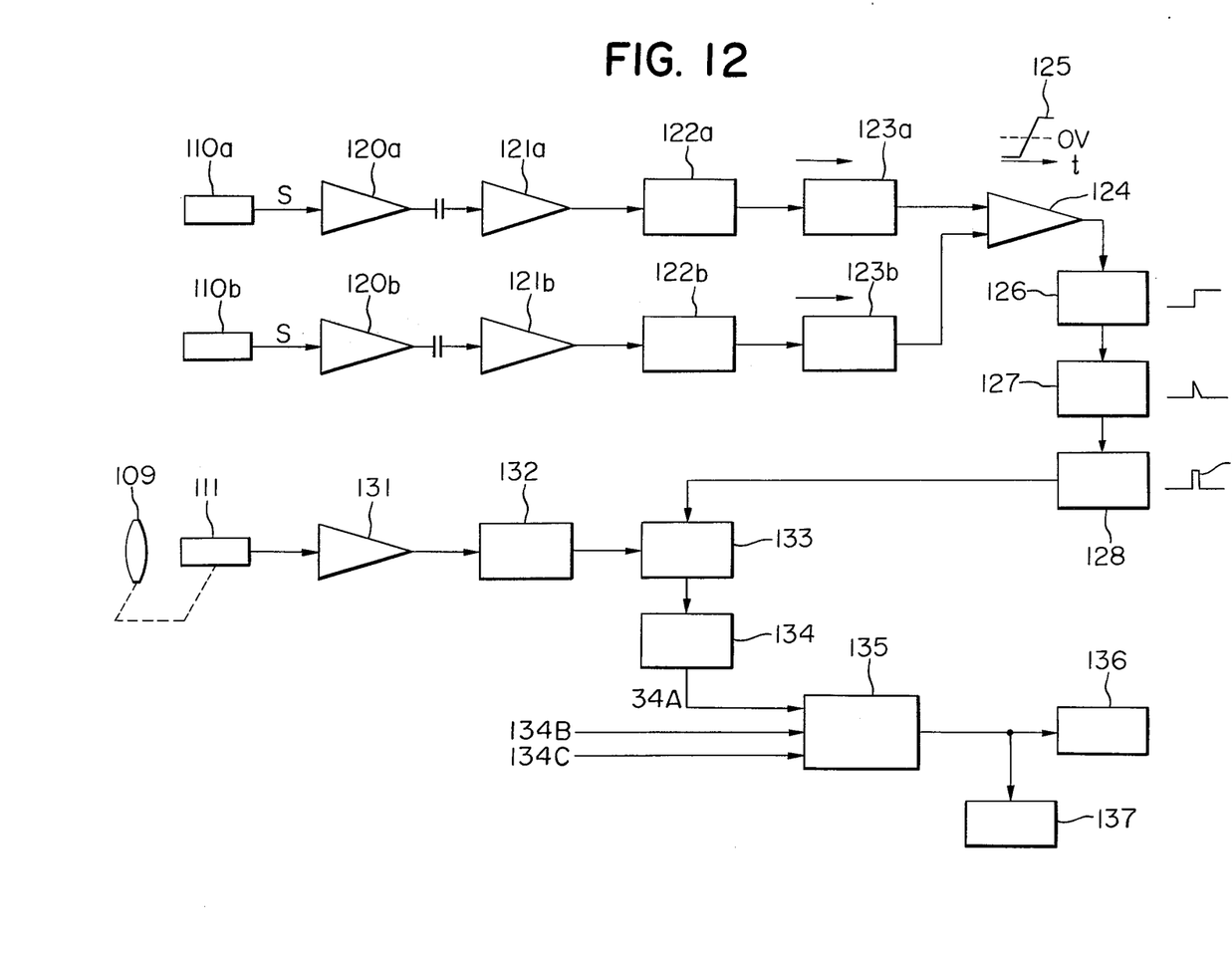
FIG. 12 is a block diagram showing the signal processing in the embodiment of FIG. 5.

FIG. 12 is a block diagram showing an example of the signal processing.

The signals from the light receiving elements 110a and 110b are respectively applied to preamplifiers 120a and 120b. The outputs of the preamplifiers 120a and 120b are capacity-coupled to amplifiers 121a and 121b, respectively, and applied to band-pass filters 122a and 122b, respectively. In these amplification stages, only the side band of the signal resulting from the displacement of the elements of the optical system including the carrier wave frequency is passed to derive a useful signal and undesirable components such as the DC component from the ambient light and the frequency component of the commercially available power source may be removed. Also, the outputs of filters 122a and 122b are detected by demodulators 123a and 123b, respectively.

Here, if the gains of the amplifiers of the demodulators 123a and 123b from the light receiving elements 110a and 110b are pre-regulated to entirely identical levels, the outputs of the demodulators 123a and 123b provide an entirely equal voltage level at the position of the relay lenses 106 and 109 whereat the bottom of the eye to be inspected and the multi-slit mask 104 satisfy the optical conjugate condition. Accordingly, the outputs of the respective demodulators including the visibility information are differentially amplified by a differential amplifier 124 and the difference therebetween is taken and at the extreme value of the visibility, there is obtained a signal 125 whose output voltage level is always zero. Here, even if the illumination level on the light receiving elements are varied by the individual differences in the reflection factor and transmittivity of the eye being inspected, the difference signal alway becomes a constant value of zero at the extremal value of the visibility.

The signal 125 is further applied as input to a comparator 126 to quantize the information on the extremal value of the visibility with respect to the time axis and produce a sampling pulse 129 of the visibility position from a pulse generator 128 through a differentiator 127. On the other hand, the visibility signal is detected by a potentiometer 111 (FIG. 5) mechanically coupled to the relay lens 109 and following the movement of the relay lens 109. In this case, the output of the potentiometer 111 is in non-linear relationship with the variation in the optical visibility and therefore, the output of the amplifier 131 is applied to a non-linear amplifier to be subjected to non-linear correction in order that, for the mechanical displacement of the relay lens 109, the displacement of the extremal value of the optical visibility thereof may be converted into a linear output. The analog output so corrected linearly as a function of the visibility waits for a sampling pulse 129 from the pulse generator and the analog signal of the extremal value in the direction of the meridian Ra of the visibility of the eye being inspected is held by a sampling circuit 133. The hold output from the sampling circuit 133 is obtained as a digital quantity through an analog/digital converter 134 as a visibility value measured in a single meridian direction by a single instantaneous measurement. The values of 124B and 124C in the other meridian direction likewise processed are applied to a digital computer 135 with the aforementioned digital value. The computer 135 calculates A·α·B by inserting the values of three D's and $\theta$ in equation $D = A \sin(2\theta + \alpha) + B$ and delivers the information thereof to a display 136 and a print-out 137 to effect the display thereof. Note that the non-linearity correction by 132 may be processed within the computer 135 or the digital computer may be replaced by an analog computer.

Figure 13:
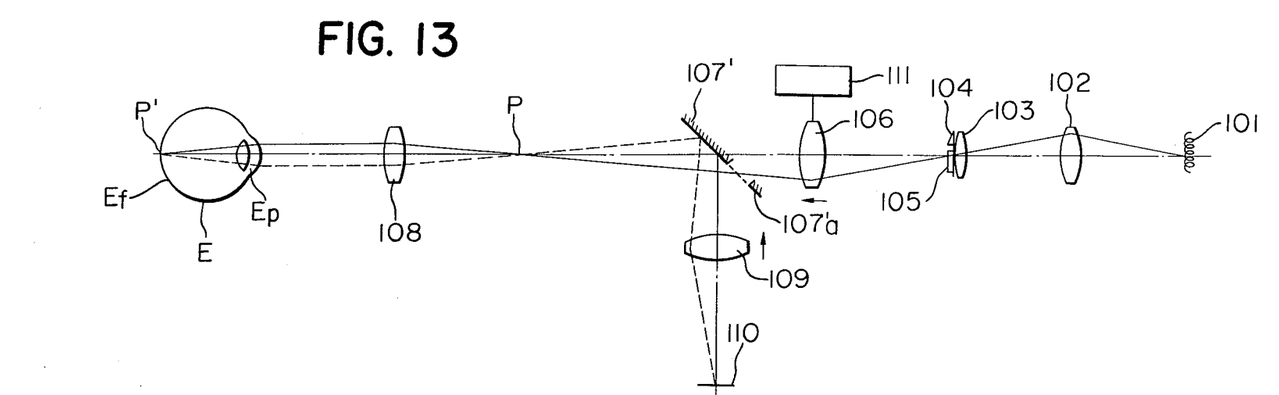
FIG. 13 is a cross-sectional view showing a fourth specific embodiment of the present invention.
Figure 14:
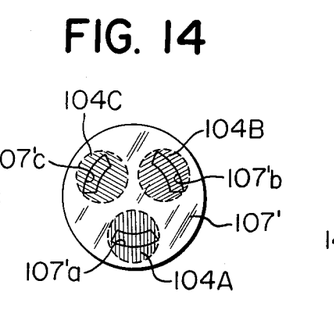
FIG. 14 is a plan view of a beam selective mirror having three openings.

FIG. 13 shows a further embodiment of the present invention, in which the members similar to those in the embodiment of FIG. 5 are given similar reference characters and the light beam here only shows the conjugate relationship. Designated by 107' is a mirror also serving to separate the light beams from one another, and FIG. 14 shows the configuration of the mirror 107' as seen in the direction of the optic axis thereof. Denoted by 107'a, 107'b and 107'c are openings formed through the mirror. The hatched portions indicate the areas illuminated by the light beams passed through the slits.

In the present embodiment, the condenser lens 102, the field lens 103, the relay lens 106 and the objective lens 108 are disposed with their optic axes coincident, and the reflecting surface of the mirror 107' is disposed so as to be inclined with respect to the optic axis, and the relay lens 109 is disposed conjugately with the optic axis.

The relay lenses 106 and 109 are movable in the direction of the optic axis, and these relay lenses 106 and 109 are moved at the same time such that the multislit mask 4 and the movable point P are conjugate with respect to the relay lens 106 and that the movable point P and the detector device 110 are conjugate with respect to the relay lens 109. The arrangement in which the movable point P is coincident with the focal point of the objective lens 108 is the reference condition.

With such an arrangement, the light beam from the light source 101 is converged by the condenser lens 102 and illuminates each slit in the multi-slit mask 104 through the field lens 103. The light beams emergent from the slits are refracted in meridian directions by the prism 105 and sufficiently separated from one another and then converged by the relay lens 106, whereafter those light beams pass through the openings 107'a, 107'b and 107'c of the mirror 107' and form images of the slits on a plane containing the point P, and then the light beams enter the objective lens 108, from which the light beams emerge as a parallel beam when the system is in its reference condition, and the parallel beam enters the eye E to be inspected and is converged by the refractive power of the eye and formed as an image on the plane containing the point P'. If the eye E is an ideal one, the point P' is coincident with the bottom of the eye, but if the eye has a refractive error, the point P' is formed at a position corresponding to the front or the rear of the eye bottom. Thus, the operator moves the relay lenses 106 and 109 and detects from the output of the detector device 110 when the multislit mask 104 and the eye bottom and the eye bottom and the detector device 110 become conjugate, and the potentiometer 111 detects the position of the relay lens 106 at that point of time, thereby calculating out the degree of astigmatism, the average visibility and the direction of astigmatism by the method of process as shown in FIG. 12.

Figure 15:
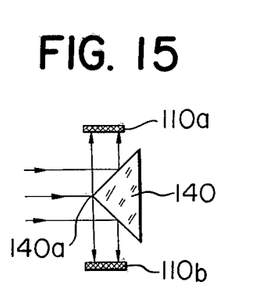
FIG. 15 is a side view showing an example of the components of the beam detecting device.
Figures 16, 18:
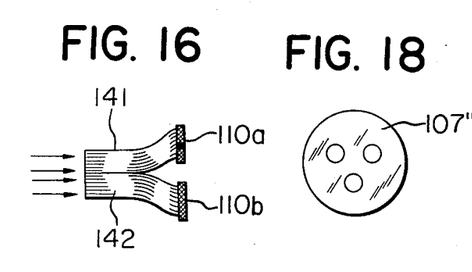
FIG. 16 is a side view showing another example of the components of the beam detecting device.
FIG. 18 is a plan view of a beam selective mirror.

FIGS. 15 and 16 respectively show modified forms of the light receiving portion of the detector device. The reason for such modified forms is to prevent the portion which cannot be measured from remaining between the two light receiving elements when the light receiving elements forming each set are brought close to each other.

In FIG. 15, the reference characters 110a and 110b designate light receiving elements, and 140 denotes a small rectangular prism whose vertical edge 140a is disposed at a predetermined position so as to be orthogonal with the meridian, and the light receiving elements 110a and 110b are provided at such a position as would be determined by the sloped surfaces of the prism. Thus, the light beam directed toward the prism is sharply split by the vertical edge of the prism and the light beams reflected by the sloped surfaces of the prism impinge on the light receiving elements.

Designated by 141 and 142 in FIG. 16 are optical fiber bundles of rectangular cross-section. These optical fiber bundles have the longer sides of their entrance ends brought close together and they are provided in place such that the joint line therebetween is orthogonal to the meridian. Light receiving elements are attached to the other ends of the fiber bundles. Thus, the light beam directed toward the entrance ends of the optical fiber bundle is split by the joint line and the light beams having entered the fiber bundle are propagated through the fiber toward the light receiving elements.

Note that a plurality of such light receiving portions as shown in FIGS. 15 and 16 are provided in the detector device.

Figure 17:
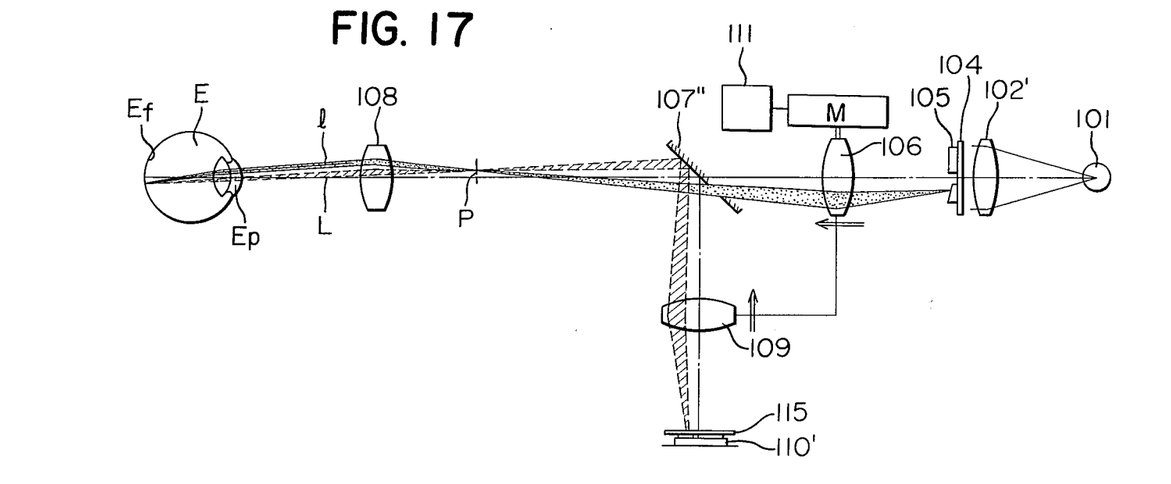
FIG. 17 is a cross-sectional view of a fifth specific embodiment of the present invention.
Figure 19:
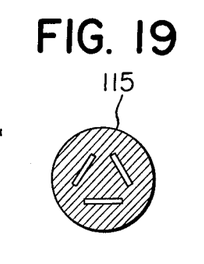
FIG. 19 is a plan view of a multi-slits mask.
Figure 20:
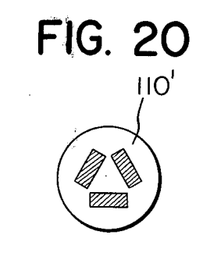
FIG. 20 is a plan view of a beam detecting device.

FIG. 17 shows a further embodiment of the present invention. In this Figure, the members similar to those in the previous embodiments are given similar reference characters. Denoted by 102' is a condenser lens, and 107" a mirror. As shown in the plan view of FIG. 18, the beam splitter 107" comprises a mirror portion and three openings which are set to correspond to the three radial lines in the multislit mask, and only the light beam emergent from a particular slit is passed through the opening. Denoted by 115 is an inspecting mask having three slit-like openings similar to those in the multislit mask 104. Numeral 110' designates a detector device whose plan view is shown in FIG. 20. The hatched portions in FIG. 20 are light receiving elements which are dimensioned slightly greater than the openings in the inspecting mask 115. The detector device is disposed such that these light receiving elements are close to just below the openings in the mask.

A light source 101 and a mirror 107" are conjugate with respect to the condenser lens 102" and the relay lens 106 in the reference condition, and the mirror 107" and the pupil or retina of the eye to be inspected are substantially conjugate with respect to the objective lens 108. Further, the multislit mask 104 is substantially conjugate with a plane containing the point P with respect to the movable relay lens 106, and the plane containing the point P is maintained such that it is conjugate with the mask 115 with respect to the relay lens 109.

The above-described apparatus is set and the subject is caused to watch a fixed target, not shown.

The light beam from the light source 101 is condensed by the condenser lens 102' and illuminates the multi-slit mask 104. Although three light beams are emergent from the slits the multi-slit mask, only one of them is shown in the drawing.

The light beams passed through the slits are refracted by the prism pillar 105 and enter the relay lens 106, by which the light beams are converged and then passed through the openings in the mirror 107" and formed as images. Thereafter, the light beams are diverged and then converged by the objective lens 108, whereafter the light beams are directed toward the eye E to form clear or blurred images on the eye bottom Ef. The light beams scatterd and reflected by the eye bottom are emergent from the eye and converged by the objective lens 108, whereafter the diverged light beams are emitted from the emitting surface of the mirror 107" toward the relay lens 109, by which the beams are converged so that clear or blurred images of the three slits formed on the eye bottom Ef are formed on the mask 15.

These light beams forming the images of the multiple slits are passed through the openings of the mask to the light receiving elements of the detector device 110' and the light receiving elements put out electrical signals corresponding to the quantities of incident light.

Therefore, when the moving mechanism M is driven to monotonously displace relay lenses 106 and 109 in the direction of the optic axis, the outputs of the light receiving elements of the detector device 110' are varied so that the peak of the output of each light receiving element is detected the from-time-to-time position of the relay lenses is detected by the position detecting device 111 to calculate out the spherical visibility, the degree of astigmatism and the astigmatism axis in accordance with the values of the positions corresponding to the directions of the meridians.

Figure 21:
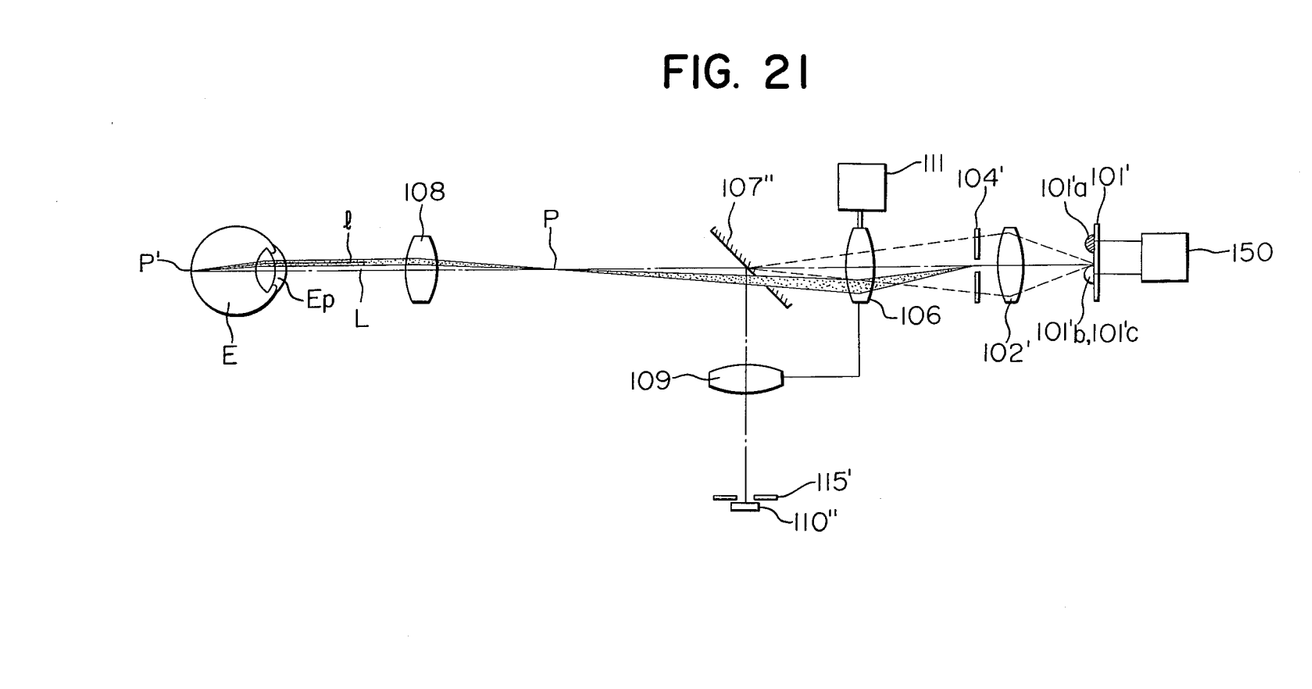
FIG. 21 is a cross-sectional view showing a sixth specific embodiment of the present invention.
Figure 22:
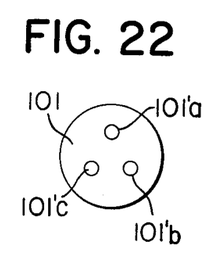
FIG. 22 is a plan view showing multiple light sources.
Figure 23:
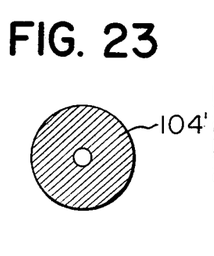
FIG. 23 is a plan view of a test mask.

FIG. 21 shows a further embodiment of the present invention. The light source portion 101' comprises three light sources 111'a, 111'b and 111'c of good flickering response characteristic such as infrared emitting diodes arranged in accordance with the radii forming 120° with each other, as depicted in FIG. 22. Designated by 102' is a condenser lens, and 104' a measurement index mark plate. The index mark plate 104' has a circular opening centrally thereof as shown in the plan view of FIG. 23. Designated by 107" is a beam selective mirror having a construction equivalent to that of the mirror shown in FIG. 18. Denoted by 115' is a mask which is a member equivalent to the index mark plate 104'. Numeral 110" designates a detector device having a light receiving area dimensioned somewhat greater than the circular opening of the mask 115'. In FIG. 21, the index mark plate 104' and the point P are always conjugate with respect to the relay lens 6, and the mask 115' and the point P are always conjugate with respect to the relay lens 109, as in the previous embodiment.

Also, when the subject is caused to occupy his predetermined position, the pupil Ep of the eye to be inspected and the reflecting surface of the mirror 107" are substantially conjugate with respect to the objective lens 108.

Designated by 150 is a light source driving circuit having the function of periodically turning on and off the light sources 111'a, 111'b and 111'c. The speed of the turn on and off is much higher than the velocity of movement of the relay lens and is set such that, when an ideal eye having no astigmatism is measured, the difference between the measurement value by the first light source and the measurement value by the second light source corresponding to another meridian is below the measurement allowance.

Now, assume that the light source 111'a has been turned on. The light emitted therefrom illuminates the opening of the index mark plate 104' through the condenser lens 102'. The light beam passed through the circular opening of the index mark plate is converged by the relay lens 106, whereafter it is passed through an opening in the beam selective mirror 107" for convergence. The converged light beam forming the image of the opening of the index mark plate is diverged and enters the back surface of the objective lens 108 and converged thereby and leaves the same, whereafter the light beam impinges on the eye to be inspected and forms clear or blurred image of the opening of the index mark plate at the eye bottom.

The light beam reflected by the eye bottom emerges from the eye to enter the objective lens 108 and is converged thereby, whereafter the light beam is diverged and reflected by the reflecting surface of the mirror 107" and converged by the relay lens 109, whereafter the light beam again forms the image on the eye bottom on the mask 115'.

If the image of the opening of the index mark plate formed on the mask 115' is blurred, the quantity of light entering the light receiving element is decreased as compared with the quantity of light when the image of the opening is clear, and the index mark plate and the mask become conjugate with the eye bottom at a point of time whereat the quantity of light exhibits a peak value.

In the present embodiment, the image of the opening which is the measurement pattern is formed on the optic axis and is circular but nevertheless, the central light ray l of the light beam entering the eye being inspected is spaced apart from the optic axis on the pupil, thus enabling the measurement of the refractive power in a particular meridian direction.

Figure 24:
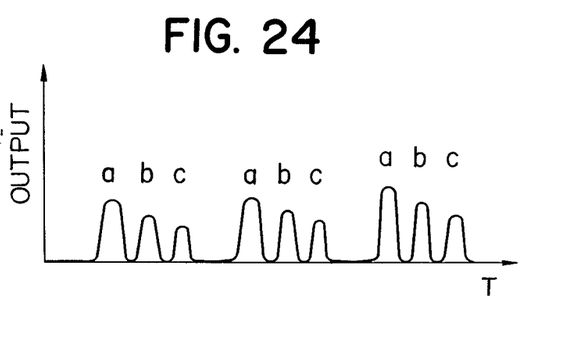
FIG. 24 shows the output signal of the photo-detector.

With such an arrangement, if the light sources 111'a, 111'b and 111'c are turned on and off periodically and the relay lenses 106 and 109 are monotonously moved in the direction of the optic axis, there is obtained such an output as shown in FIG. 24. In FIG. 24, the abscissa T corresponds to time or amount of movement of the relay lenses while the ordinate represents the outputs of the light receiving elements and three outputs a, b and c appear periodically. Thus, the time points whereat the signals a, b and c are at their peaks are detected and the refractive power corresponding to the three meridians may be measured from the value of the detected position of the relay lens at each of the time points.

According to the present invention, as has hitherto been described, the refractive powers in the directions of a plurality of meridians can be measured substantially at the same time and this reduces the errors and eliminates the error resulting from the irregular rotation because there is no rotational element. The construction is simplified and even in a construction wherein the light source is turned on and off, the absence of an optically rotative portion leads to quick change-over of the three radial line directions and minimizes the errors, if any, to less than their allowed levels.

What we claim is:

1. An eye refractometer, comprising: a projection system having test pattern generating means for generating test beams and having slits in three meridians arranged in the illumination path such that three test marks are projected into the eye and projection optical means for projecting said test beams to an eye to be inspected and forming an image of the test pattern corresponding to each of the meridians;

an inspecting system having beam detecting means for independently detecting the test beams from the eye to be inspected, and inspecting optical system for transmitting the beams to said beam detecting means;

focus adjusting means coupled to said projection system and said inspecting system for focusing of said two systems; and beam splitting means for optically coupling said projection optical system and said inspecting optical system.

2. A refractometer according to claim 1, wherein said test pattern generating means includes a radiation source and test pattern supporting means for supporting test patterns related to each of at least three meridians.

3. A refractometer according to claim 2, wherein said test pattern supporting means has on a light-intercepting plate at least one slit perpendicular to each of said meridians.

4. A refractometer according to claim 1, wherein said test pattern generating means includes a radiation source, and pattern supporting means for supporting test patterns related to each of at least three meridians, and said beam detecting means has detecting areas corresponding to said test patterns.

5. A refractometer according to claim 4, wherein each of said detecting areas comprises a photoelectric cell.

6. A refractometer according to claim 4, wherein each of said detecting areas comprises two sub-areas disposed parallel to said meridian.

7. A refractometer according to claim 4, wherein each of said sub-areas comprises a photoelectric cell.

8. A refractometer according to claim 4, wherein each of said sub-areas comprises the input terminal of a light guiding means, and a photoelectric cell is disposed in opposed relationship with the output terminal of said light guiding means.

9. A refractormeter according to claim 4, wherein a reflecting member for reflecting the beam toward a photoelectric cell is disposed behind said sub-area.

10. A refractometer according to claim 1, wherein said test pattern generating means includes at least three beam sources disposed equidistantly from the optic axis, drive means for selectively turning on one of said beam sources, and test pattern supporting means for supporting a test pattern on the optic axis, and said beam detecting means has a detecting area containing the optic axis.

11. A refractometer according to claim 10, wherein said beam detecting means comprises a mask having openings corresponding to said test patterns, and a photoelectric cell disposed behind said mask.

12. A refractometer according to claim 1, wherein said projection optical means includes movable lens means movable in the direction of the optic axis, and said focus adjusting means moves said movable lens means in one direction during one measurement.

13. A refractometer according to claim 1, wherein said projection optical means includes first movable lens means movable in the direction of the optic axis, said inspecting optical means includes second movable lens means movable in the direction of the optic axis, said focusing means moves said first and second movable lens means in one direction during one measurement, said test pattern generating means includes a radiation source and test pattern supporting means for supporting test patterns related to each of at least three meridians and said beam splitting means has a mirror having at least one opening.

14. An eye refractometer comprising:
an objective optical means opposed to an eye to be inspected;
reflecting means having a reflecting surface inclined with respect to the optic axis of said objective optical means and at least one opening formed through said reflecting surface, said reflecting means being effective to split said optic axis into two;
first and second lens means aligned with two optic axes and movable in the direction of the optic axis;
focus adjusting means for moving said first and second lens means;
position detecting means for detecting the position of said lens means on the optic axis;
a test marker aligned with one of said optic axes and having slits in three meridians arranged in the illumination path such that three test marks are projected into the eye;
a beam source;
a condensing optical means for condensing the beam from said beam source onto said test marker; and
a beam detecting device aligned with the remaining one of said optic axes for detecting the image of said test mark reflected on the retina of said eye.

15. A refractometer according to claim 14, wherein the opening of said reflecting means is conjugate with the front part of said eye with respect to said objective optical means.

16. A refractometer according to claim 14, wherein said beam detecting device has at least three sets of photoelectric cells forming a borderline intersecting each of the meridians passing through the center thereof.

17. A refractometer according to claim 14, wherein said beam detecting device has a mask having at least one slit intersecting each of the meridians passing through the center thereof, and photoelectric cells disposed behind each of said at least one slit.

18. A refractometer according to claim 16 or 17, wherein said photoelectric cells have sensitivity to infrared light.

19. An eye refractometer comprising:
objective optical means opposed to an eye to be inspected;
reflecting means having a reflecting surface inclined with respect to the optic axis of said objective optical means and at least one opening formed through said reflecting surface, said reflecting means being effective to split said optic axis into two;
first and second lens means aligned with said two optic axes and movable in the direction of the optic axis;
focus adjusting means for moving said first and second lens means;
position detecting means for detecting the position of said lens means on the optic axis;
a test marker having a test mark on one of said two optical axes;
at least three fixed directional beam sources disposed equidistantly from said one of the two optical axes for selectively illuminating said test mark; and
beam detecting device aligned with the remaining one of said optic axes for detecting the image of the test mark of said test marker reflected on the retina of the eye to be inspected.

20. A refractometer according to claim 19, wherein said beam detecting device has a mask having an opening containing the optic axis, and a photoelectric cell disposed behind the mask.

21. A refractometer according to claim 20, wherein said photoelectric cell has sensitivity to infrared light.

22. A refractometer according to claim 1, further comprising direction selecting means disposed in said projection system for controlling the directions of travel of said test beams to space apart from each other the points whereat the central ray of each of said beams passes through the pupil of the eye to be inspected.

23. An eye refractometer comprising:
a first system including a test marker having a test mark corresponding to each of at least three meridians, illuminating means for illuminating said marker and projection optical means for projecting images of test marks;
a second system including photodetecting means having at least three detecting areas, and also including imaging optical means for imaging images of the test marks reflected by a fundus of an eye to be inspected on said detecting areas; and
focus adjusting means coupled to said first and second systems for focusing of said two systems on the fundus of the eye to be inspected.

24. A refractometer according to claim 23, wherein said detecting areas each include two radially disposed sub-areas.

25. A refractometer according to claim 24, wherein said photodetecting means includes at least three marks each provided with an opening, and at least three photocells.

26. An eye refractometer comprising:
a first system including a test marker having one mark on the optical axis thereof, illuminating means for illuminating said mark selectively in at least fixed three meridians, projection optical means for projecting said mark, and beam limiting means, optically conjugate with an anterior portion of an eye to be inspected, for limiting a projection beam;
second system including photodetecting means, having one detecting area on the optical axis thereof for generating a first electric signal and imaging optical means for forming an image of the mark on said detecting area;

focus adjusting means coupled to said projection system and said inspecting system for focusing of said two systems;

focus detecting means coupled with one of said systems for generating a second electrical signal; and circuit means for calculating a refraction power corresponding to each of said three meridians by said first and second electric signals.

* * * * *

UNITED STATES PATENT AND TRADEMARK OFFICE
CERTIFICATE OF CORRECTION

PATENT NO. : 4,293,198
DATED : October 6, 1981
INVENTOR(S) : YOSHIMI KOHAYAKAWA, ET AL.

It is certified that error appears in the above—identified patent and that said Letters Patent is hereby corrected as shown below:

Column 2, line 47, change "beem" to --been--.
Column 10, line 31, change "scatterd" to --scattered--.

Claim 9, line 1 (column 12, line 61), "refractor-meter" should be --refractometer--.
Claim 26, line 4 (column 14, line 59), "fixed three" should be --three fixed--.

Signed and Sealed this

Twenty-sixth Day of January 1982

[SEAL]

Attest:

GERALD J. MOSSINGHOFF

Attesting Officer

Commissioner of Patents and Trademarks